United States Patent [19]

Dimmig

[11] 4,140,604

[45] Feb. 20, 1979

[54] PROCESS FOR PREPARING MERCAPTANS

[75] Inventor: Daniel A. Dimmig, King of Prussia, Pa.

[73] Assignee: Pennwalt Corporation, Philadelphia, Pa.

[21] Appl. No.: 921,693

[22] Filed: Jul. 3, 1978

[51] Int. Cl.² .............................................. B01J 1/10
[52] U.S. Cl. ............................ 204/158 R; 204/162 R
[58] Field of Search ........................ 204/158 R, 162 R

[56] References Cited

U.S. PATENT DOCUMENTS 3,248,315  4/1966  Warner et al. .................... 204/162 R
4,052,283  10/1977  Dannels ........................... 204/158 R

*Primary Examiner*—Howard S. Williams

[57] ABSTRACT

An improvement in the process for preparing mercaptans wherein an ethylenically unsaturated organic compound is reacted with hydrogen sulfide that is present in molar excess, catalyzed by UV light, with recovery of the desired mercaptan from the reaction mixture. The improvement being the carrying out of the reaction in the presence of an effective amount of selected class of acetophenone reaction promoters. The improved process results in much faster reaction rates.

8 Claims, No Drawings

PROCESS FOR PREPARING MERCAPTANS

BACKGROUND OF THE INVENTION

This invention relates to the process for preparing a mercaptan by the reaction of an ethylenically unsaturated compound with an excess of hydrogen sulfide in the presence of ultraviolet light (UV) as a catalyst. The method of this invention involves the inclusion of a certain class of acetophenone derivatives with the reactants to provide much faster reaction rates.

Organic sulfur compounds, e.g., mercaptans, are of considerable commercial importance. A convenient and potentially economical process for the production of mercaptans involves the addition of hydrogen sulfide to ethylenically unsaturated compounds in the presence of ultraviolet radiation. The reaction can be carried out in a batch or a continuous manner. Relatively high molar ratios of hydrogen sulfide to the unsaturated compound are required to obtain high yields of the desired mercaptan.

Ultraviolet light from a mercury arc is a very effective catalyst for the addition of hydrogen sulfide to a double bond (Reid, "Organic Chemistry of Bivalent Sulfur", Volume 1, pg. 21). In the presence of ultraviolet light, a relatively fast reaction is observed with the addition of hydrogen sulfide to propylene and butene-1. However, the rate of reaction of hydrogen sulfide with an olefin is known to decrease significantly with an increase in the molecular weight of the olefin.

This invention provides an improved method for the preparation of mercaptans by the reaction of hydrogen sulfide with ethylenically unsaturated compounds in the presence of ultraviolet radiation. Another object is to provide a method for the preparation of mercaptans characterized by a marked increase in the rate of reaction of hydrogen sulfide with the ethylenically unsaturated compound.

The reaction of this invention involves the "inverse" or non-Markownikoff reaction of hydrogen sulfide with an olefin. In the ionic (acid or base) catalyzed reaction, addition across the olefinic linkage takes place according to the Markownikoff rule, i.e., "normal" addition in which the sulfhydryl radical attaches to the unsaturated carbon atom having the lesser number of hydrogen atoms. In the reaction of this invention "inverse" or non-Markownikoff addition occurs in which the sulfhydryl radical attaches to the unsaturated carbon atom having the greater number of hydrogen atoms. This invention is especially useful for the preparation of primary mercaptans.

The reaction of an ethylenically unsaturated compound with hydrogen sulfide catalyzed by UV radiation is well known. For instance, see *Organic Chemistry of Bivalent Sulfur* Volume 1, pg. 21, E. Emmet Reid, Chemical Publishing Company, Inc., 212 Fifth Avenue, New York, N.Y., 1958.

The use of a wide range of acetophenone derivatives as photo initiators in various polymerization processes is also well known. In this regard, see U.S. Pat. No. 3,715,293 to Sander, et al, dated Feb. 6, 1973; U.S. Pat. No. 379,807 to Osburn, et al, dated Sept. 18, 1973; U.S. Pat. No. 3,050,452 to Louthan, dated Aug. 21, 1962; and U.S. Pat. No. 2,448,828 to Renfrow, dated Sept. 7, 1948.

The particular mercaptans prepared by the process of this invention have a wide range of commercial uses, which include the field of adhesives, agricultural chemicals, polymer chain stoppers, chain transfer agents, and cross linking additives, to name a few.

SUMMARY OF THE INVENTION

This invention is described as a process for preparing a mercaptan wherein an ethylenically unsaturated organic compound is reacted with hydrogen sulfide that is present in molar excess in the presence of ultraviolet radiation, and said mercaptan is recovered from the resulting reaction mixture; the improvement comprising carrying out said reaction in the presence of an effective amount of an acetophenone derivative reaction promoter of the structural formula:

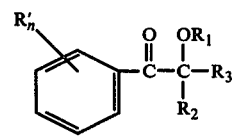

wherein $R_1$ is an alkyl group having from 1 to 10 carbon atoms; $R_2$ is a phenyl group or an alkoxy group —OR wherein R is an alkyl group having from 1 to 10 carbon atoms; $R_3$ is selected from the group consisting of hydrogen, alkyl of from 1 to 8 carbon atoms, aryl of from 6 to 14 carbon atoms or cycloalkyl of five to eight ring carbon atoms; $R'$ is an alkyl group from 1 to 4 carbon atoms, chloro, bromo or iodo and n is a whole number between zero and three.

Particularly preferred reaction promoters are those wherein in the process as defined in claim 1 wherein the structural formula $R_1$ is an alkyl group having from 1 to 4 carbon atoms, $R_2$ is phenyl or —OR wherein R is an alkyl group having 1 to 4 carbon atoms, $R_3$ is H and n is 0.

The advantages of the process are particularly apparent for the following ethylenically unsaturated compounds: ethylene, propylene, butene-1, isobutene, pentene-1, hexene-1, octene-1, decene-1, dodecene-1, tetradecene-1, hexadecene-1, octadecene-1, eicosene-1, cyclohexene, 1-methylcyclohexene, vinylcyclohexane, styrene, methyl vinyl ether, ethyl vinyl ether, diallyl ether, 4-vinylcyclohexene-1, divinyl benzene, trivinyl benzene, dipentene, d-limonene, alpha pinene, beta pinene, camphene, p-menthene, alpha terpineol, and other terpene olefins.

The molar excess of hydrogen sulfide to unsaturated reactant is preferably within the range of about 2 to 1 to about 30 to 1 for each double bond in the unsaturated reactant. The pressure must be maintained at a sufficient level to maintain the reactants in a liquid state which usually corresponds to a reaction temperature within the range of about 0° to about 70° C. and a pressure of about 250 psig to about 600 psig.

The reaction promoter is preferably present in an amount of 0.0001 to 0.1 mole per mole of olefinic compound, more preferably 0.0005 to 0.04 mole per mole of olefinic compound.

DESCRIPTION OF THE PREFERRED EMBODIMENTS

Ethylenically unsaturated compounds suitable for this reaction include ethylene, propylene, butene-1, isobutene, pentene-1, hexene-1, octene-1, decene-1, dodecene-1, tetradecene-1, hexadecene-1, octadecene-1, eicosene-1, cyclohexene, 1-methylcyclohexene, vinylcyclohexane, styrene, methyl vinyl ether, ethyl vinyl ether, diallyl ether, 4-vinylcyclohexene-1, divinyl benzene, trivinyl benzene, dipentene, d-limonene. Other operable terpene olefins, in addition to dipentene and d-limonene include alpha pinene, beta pinene, camphene, p-menthene, and alpha terpineol.

Acetophenone derivatives found to be useful in this invention are known to be good photoinitiators for the curing of certain polymers in the presence of ultraviolet radiation (wavelength of about 1800–4000 angstrom units). Compounds that promote free-radical type reactions in the presence of ultraviolet radiation manifest their activity in various ways. The compound may absorb ultraviolet radiation to form an energetic excited state with subsequent direct transfer of this energy to one or both of the reactants. Such a compound is referred to as a photosensitizer. In another case, the compound in its excited state can undergo cleavage to form free radicals which in turn initiate the desired reaction. Such a compound is referred to as a photoinitiator. Since the mode of action of the acetophenone derivatives of this invention is uncertain, any reference to these compounds will use the general term promoter.

Particularly preferred reaction promoters useful in the present invention include alpha, alpha-dimethoxyacetophenone; alpha, alpha-diethoxyacetophenone; alpha, alpha-dipropoxyacetophenone; alpha, alpha-dibutoxyacetophenone; alpha-methoxy-alpha-phenylacetophenone; alpha-ethoxy-alpha-phenylacetophenone; alpha-propoxy-alpha-phenylacetophenone; and alpha-butoxy-alpha-phenylacetophenone.

The reaction promoters are preferably added in an amount of 0.0001 to 0.1 mole per mole of olefinic compound, more preferably 0.0005 to 0.04 mole per mole of olefinic compound.

The mole ratio of hydrogen sulfide to olefin is about 2/1 to 30/1 for each double bond and preferably 3/1 to 20/1. At a ratio less than 3/1, formation of by-products such as dialkyl sulfide increases. At ratios greater than about 10/1, no further improvement in mercaptan yield is obtained and recovery costs are increased.

The reaction temperature shows little if any effect on the reaction over the range of 0° to 70° C. The preferred range is 20°–60° C.

A pressure sufficient to maintain both the hydrogen sulfide and olefin in the liquid state is used. The preferred range is 250 to 600 psig depending upon the olefin used and the reactant mole ratio. Autogenous pressures are generally satisfactory.

A number of well-known sources of the appropriate ultraviolet light are readily available. Particularly preferred is a high pressure UV mercury vapor lamp that emits UV radiation having a wavelength within the range of about 1800 to 4000 angstrom units up to about 6000 angstrom units. The earlier-mentioned U.S. Patents relating to UV radiation to facilitate polymerization reactions are also suitable in the practice of the instant invention as a UV source. For any particular reactor geometry the most effective means and efficient method and geometrical arrangement can be readily ascertained for a given UV source.

EXAMPLE 1

A mixture of 1000 g. (5.94 moles) of dodecene-1 and 1015 g. of hydrogen sulfide (29.78 moles) is charged to a 1-gallon (3.785 liters) autoclave, previously purged with nitrogen. The autoclave is equipped with a stirrer, thermocouple, and a quartz immersion well containing a high pressure mercury vapor ultraviolet light (200 watt) that emits UV radiation of a wavelength within the range of 1800–4000 angstrom units. The temperature of the mixture is raised to 45° C. and the pressure then increases to a sufficient level to maintain the reactants in a liquid state, which is about 450 psig. in this example. While continuing stirring, ultraviolet radiation is applied to the reactants. This is accomplished by starting the lamp outside of the reactor and inserting the lamp at zero reaction time. Samples of the reaction mixture are collected at 5, 10, 15, 20, and 30 minute intervals. Samples are analyzed by gas chromatography for dodecene-1, 1-dodecanethiol, isomeric dodecanethiols and n-dodecyl sulfide. The data are shown in Table 1.

EXAMPLES 2–5

In these examples, the reactions are carried out in the same manner as described in Example 1, except that the indicated amounts of the promoter, alpha, alpha-diethoxyacetophenone, are added to the reaction mixture. Experimental data are shown in Table 1.

EXAMPLES 6–9

In these examples, the reactions are carried out in the same manner as described in Example 1, except that the indicated amounts of the promoter alpha-ethoxy-alpha-phenylacetophenone, are added to the reaction mixture. Experimental data are shown in Table 1.

Table 1

| Ex. No. | Promoter | Promoter Concentration Mole % a) | Weight % Conversion to 1-Dodecanethiol at Reaction Time in Minutes | | | | |
|---|---|---|---|---|---|---|---|
| | | | 5 | 10 | 15 | 20 | 30 |
| 1 | None | | 27.7 | 48.3 | 58.1 | 63.7 | 69.6 |
| 2 | Alpha, Alpha-Diethoxyacetophenone | 0.10 | 49.4 | 63.5 | 68.9 | 71.6 | 73.8 |
| 3 | " | 0.50 | 57.4 | 69.3 | 71.7 | 74.5 | — |
| 4 | " | 1.00 | 62.7 | 73.0 | 75.6 | 76.6 | 77.5 |
| 5 | " | 2.00 | 58.9 | 70.4 | 73.9 | 75.0 | 76.2 |
| 6 | Alpha-ethoxy-alpha-phenyl acetophenone | 0.10 | 51.4 | 67.2 | 72.5 | 74.4 | 78.4 |
| 7 | " | 0.50 | 54.6 | 69.4 | 73.7 | 74.5 | 76.4 |
| 8 | " | 1.00 | 62.1 | 73.7 | 76.0 | 77.0 | 77.2 |
| 9 | " | 2.00 | 60.7 | 71.3 | 74.1 | 74.9 | 75.9 |
| 10 | "Vicure 10" b) | 1.00 | 61.3 | 72.8 | 75.5 | 76.4 | 76.8 | a) Based on dodecene-1
b) Trademark of Stauffer Chemical Company for its benzoin alkyl ether photosensitizer The data in Table 1 illustrate the unpredictable large increase in the rate of reaction of hydrogen sulfide with dodecene-1 in the presence of the acetophenone-type promoters useful in practicing the method of this invention. The most striking increase in rate is observed during the important early stages of the reaction. At promoter concentrations of 0.5 mole % or above, the conversion to 1-dodecanethiol is at least doubled at a 5 minute reaction time.

EXAMPLE 10

In this example, the reaction is carried out in the same manner as described in Example 1, except that 1 mole % of the promoter, "Vicure 10", is added to the reaction mixture. See Table 1, supra., for the results.

EXAMPLE 11

A mixture of 426 grams (3.13 moles) of d-limonene and 1605 grams (47.10 moles) of hydrogen sulfide is charged to a one gallon (3.785 liters) autoclave as described in Example 1. The temperature of the reaction mixture is raised to 40° C. With vigorous stirring, the reaction mixture is exposed to a 200-watt, mercury vapor lamp. Samples of the reaction mixture are collected at 10, 15, 20, 30 and 45 minute intervals. Samples are analyzed for d-limonene, 2- and 9-d-limonene monomercaptans, and 2, 9-d-limonene dimercaptan. Experimental data are included in Table 2.

EXAMPLES 12–15

In these examples, the reactions are carried out in the same manner as described in Example 11, except that the indicated amounts of the promoter, alpha, alpha-diethoxyacetophenone, are added to the reaction mixture. Experimental data are shown in Table 2.

EXAMPLES 16–19

In these examples, the reactions are carried out in the same manner as described in Example 11, except that the indicated amounts of the promoter, alpha-ethoxy-alpha-phenylacetophenone, are added to the reaction mixture. Experimental data are shown in Table 2.

EXAMPLE 20

In this example, the reaction is carried out according to Example 11, except that the indicated amount of the promoter, "Vicure 10," (trademark of Stauffer Chemical Company's benzoin alkyl ether photosensitizer) is added to the reaction mixture. See Table 2.

Examples 21–24 are repeated except that the ethylenically unsaturated reactant is d-limonene. Similar increases in reaction rates occur.

Examples 21–24 and the experiments of the foregoing paragraph are repeated except that $R_2$ is phenyl and $R_1$ is consecutively varied from methyl, propyl, and butyl. Similar increases in reaction rates occur.

Examples 21–24 and the experiments of the foregoing two paragraphs are repeated except that the following reactants are substituted consecutively: butene-1, octene-1, octadecene-1, methyl vinyl ether, diallyl ether, 4-vinylcyclohexene-1, beta pinene, and alpha terpineol.

I claim:

1. In a process for preparing a mercaptan wherein an ethylenically unsaturated organic compound is reacted with hydrogen sulfide that is present in molar excess in the presence of ultraviolet radiation, and said mercaptan is recovered from the resulting reaction mixture; the improvement comprising carrying out said reaction in the presence of an effective amount of an acetophenone derivative reaction promoter of the structural formula:

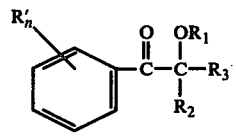

wherein $R_1$ is an alkyl group having from 1 to 10 carbon

Table 2

| Example Number | Promoter | Promoter Concentration Mole % a.) | Weight % Conversion to d-Limonene dimercaptan at Reaction Time in Minutes | | | | |
|---|---|---|---|---|---|---|---|
| | | | 10 | 15 | 20 | 30 | 45 |
| 11 | None | 0 | 0.6 | 0.9 | 1.8 | 4.7 | 17.7 |
| 12 | Alpha, Alpha-Diethoxyacetophenone | 0.10 | 2.3 | 2.5 | 5.0 | 14.6 | 38.4 |
| 13 | " | 0.50 | 4.9 | 17.3 | 39.7 | 69.9 | 84.3 |
| 14 | " | 1.00 | 6.5 | 23.5 | 49.6 | 76.9 | 88.0 |
| 15 | " | 2.00 | 5.5 | 26.7 | 53.4 | 63.2 | 91.9 |
| 16 | Alpha-ethoxy-alpha-phenyl-acetophenone | 0.10 | 4.0 | 12.4 | 27.6 | 57.2 | 78.4 |
| 17 | " | 0.50 | 11.1 | 40.4 | 69.2 | 87.2 | 92.2 |
| 18 | " | 1.00 | 7.6 | 27.0 | 61.5 | 87.4 | 93.4 |
| 19 | " | 2.00 | 5.5 | 18.9 | 55.4 | 87.9 | 93.4 |
| 20 | Vicure 10 | 2.00 | 8.1 | 39.3 | 76.8 | 91.6 | 93.1 | a.) Based on d-Limonene

The data of Table 2 show that when the reaction of $H_2S$ with d-limonene is carried out in the presence of a reaction promoter in accordance with this invention, the rate of conversion to d-limonene dimercaptan is much greater than that obtained by carrying out the reaction in the absence of the promoter.

EXAMPLES 21–24

The procedures of Examples 1–9 are repeated except that the reaction promoter is varied consecutively as shown in Table 3 below. The references are to the structural formula as shown in the "Summary of Invention."

Increases in reaction rates similar to those of Examples 2–9 are observed.

Table 3

| Example | $R_1$ | $R_2$ | R | $R_3$ | R' | n | Reactant |
|---|---|---|---|---|---|---|---|
| 21 | ethyl | OR | ethyl | H | chloro | 1 | dodecene-1 |
| 22 | " | " | " | H | chloro | 2 | " |
| 23 | " | " | " | H | bromo | 1 | " |
| 24 | " | " | " | phenyl | — | 0 | " | atoms; $R_2$ is a phenyl group or an alkoxy group —OR wherein R is an alkyl group having from 1 to 10 carbon atoms; $R_3$ is selected from the group consisting of hydrogen, alkyl of from 1 to 8 carbon atoms, aryl of from 6 to 14 carbon atoms or cycloalkyl of five to eight ring carbon atoms; R' is an alkyl group of from 1 to 4 carbon atoms, chloro or bromo and n is a whole number between zero and three.

2. The process as defined in claim 1 wherein in the structural formula $R_1$ is methyl or ethyl, $R_2$ is phenyl or —OR wherein R is methyl or ethyl, $R_3$ is H and n is O.

3. The process as defined in claim 1 wherein the ethylenically unsaturated organic compound is octene-1, dodecene-1 or d-limonene and the acetophenone derivative reaction promoter is alpha, alpha-diethoxyacetophenone.

4. The process as defined in claim 1 wherein the ethylenically unsaturated organic compound is octene-1, dodecene-1, or d-limonene and the acetophenone derivative reaction promoter is selected from the group consisting of alpha-ethoxy-alpha phenylacetophenone, alpha-propoxy-alpha-phenylacetophenone, alpha-butoxy-alpha-phenylacetophenone, and mixtures thereof.

5. The process as defined in claim 1 wherein the ethylenically unsaturated organic compound is selected from the group consisting of ethylene, propylene, butene-1, isobutene, pentene-1, hexene-1, octene-1, decene-1, dodecene-1, tetradecene-1, hexadecene-1, octadecene-1, eicosene-1, cyclohexene, 1-methylcyclohexene, vinylcyclohexane, styrene, methyl vinyl ether, ethyl vinyl ether, diallyl ether, 4-vinylcyclohexene-1, divinyl benzene, trivinyl benzene, dipentene, d-limonene, alpha pinene, beta pinene, camphene, p-menthene, and alpha terpineol.

6. The process as defined in claim 1 wherein the molar ratio of hydrogen sulfide to each double bond of the ethylenically unsaturated organic compound is in the range of about 2 to 1 to about 30 to 1 for each double bond.

7. The process as defined in claim 1 wherein the ethylenically unsaturated hydrocarbon compound and the hydrogen sulfide are reacted at a temperature within the range of about 0°–70° C. and the pressure of the reaction is maintained within the range of about 250 psig to about to about 600 psig to maintain the reactants in a liquid state.

8. The process as defined in claim 1 wherein the reaction promoter is present in an amount of 0.0001 to 0.1 mole per mole of ethylenically unsaturated compound.

* * * * *